United States Patent [19]

Shaw, Jr.

[11] 4,097,151

[45] Jun. 27, 1978

[54] METHOD OF AND APPARATUS FOR LOCATING B TYPE AND POINT TYPE DEFECTS IN A GLASS RIBBON

[75] Inventor: Hugh E. Shaw, Jr., New Kensington, Pa.

[73] Assignee: PPG Industries, Inc., Pittsburgh, Pa.

[21] Appl. No.: 667,325

[22] Filed: Mar. 16, 1976

[51] Int. Cl.² ...................... G01N 21/00; G01N 21/16
[52] U.S. Cl. .................................. 356/73; 250/572; 356/200
[58] Field of Search ................. 356/73, 199, 200, 239; 250/563, 572

[56] References Cited

U.S. PATENT DOCUMENTS

| | | | |
|---|---|---|---|
| 3,199,401 | 8/1965 | Sleighter et al. ...................... | 356/200 |
| 3,202,043 | 8/1965 | Galey et al. .......................... | 356/200 |
| 3,609,380 | 9/1971 | Shaw, Jr. .............................. | 356/239 |
| 3,871,773 | 3/1975 | Shaw, Jr. .............................. | 356/200 |

FOREIGN PATENT DOCUMENTS 906,947  9/1962  United Kingdom ................. 356/200

*Primary Examiner*—Vincent P. McGraw
*Attorney, Agent, or Firm*—Donald Carl Lepiane

[57] ABSTRACT

A beam of light is transmitted through a glass ribbon along a scan path onto a beam splitter. The beam splitter directs a first scanning beam onto a first detector responsive to B type defects and a second scanning beam onto a second detector responsive to point type defects. Monitoring the movement of the scanning beam and the signals from the detectors, the location of B type and point type defects in a glass ribbon are obtained.

13 Claims, 19 Drawing Figures

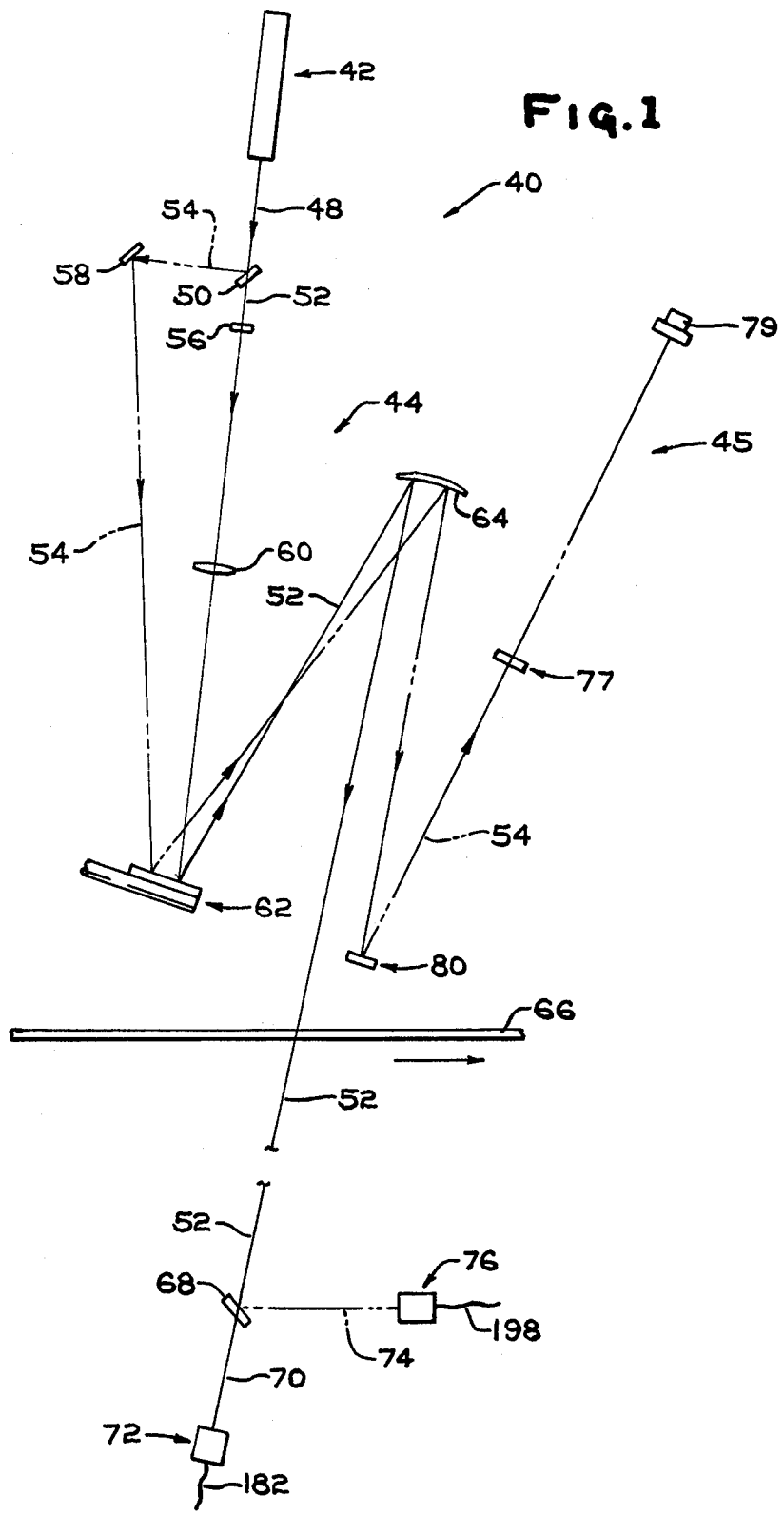

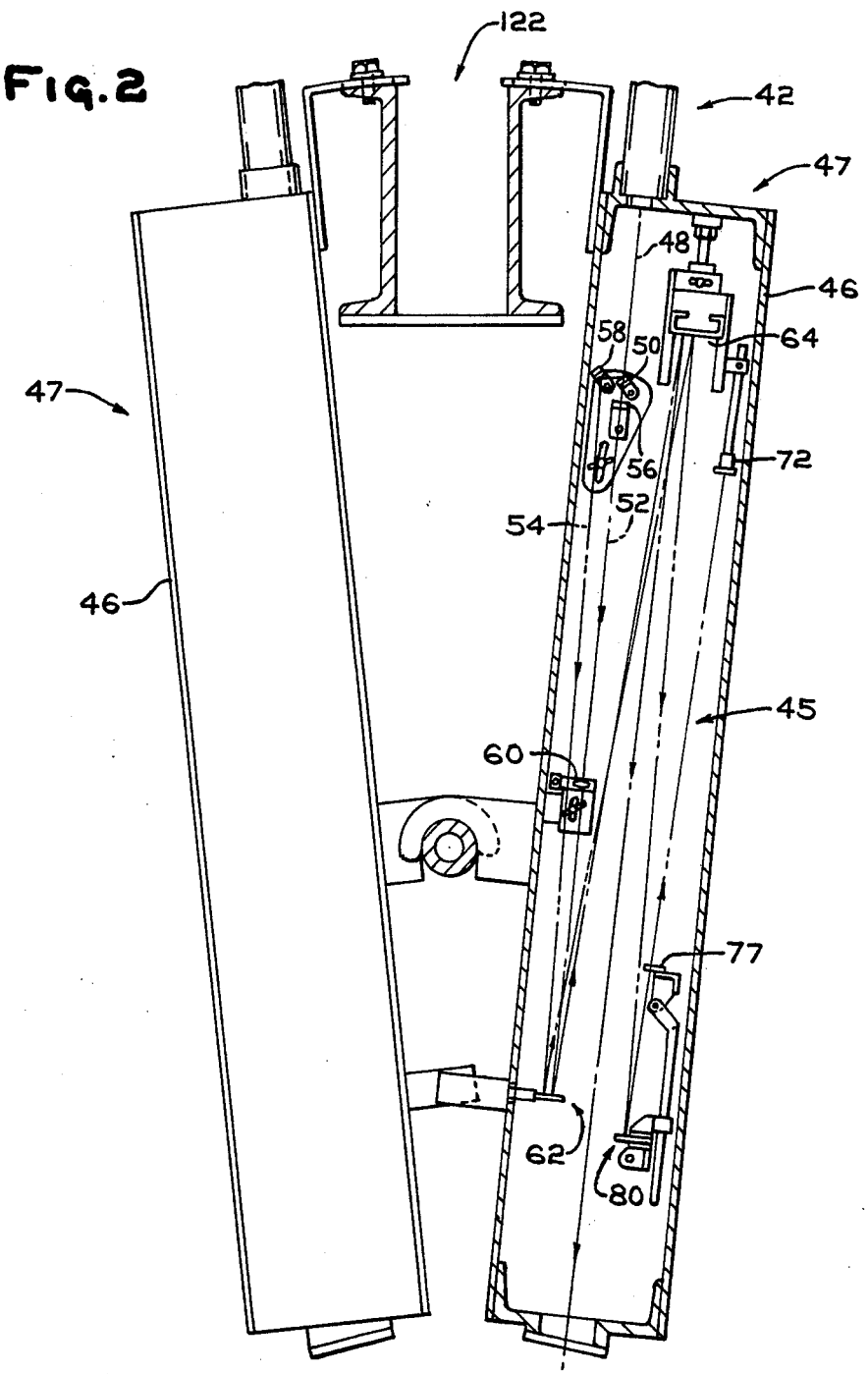

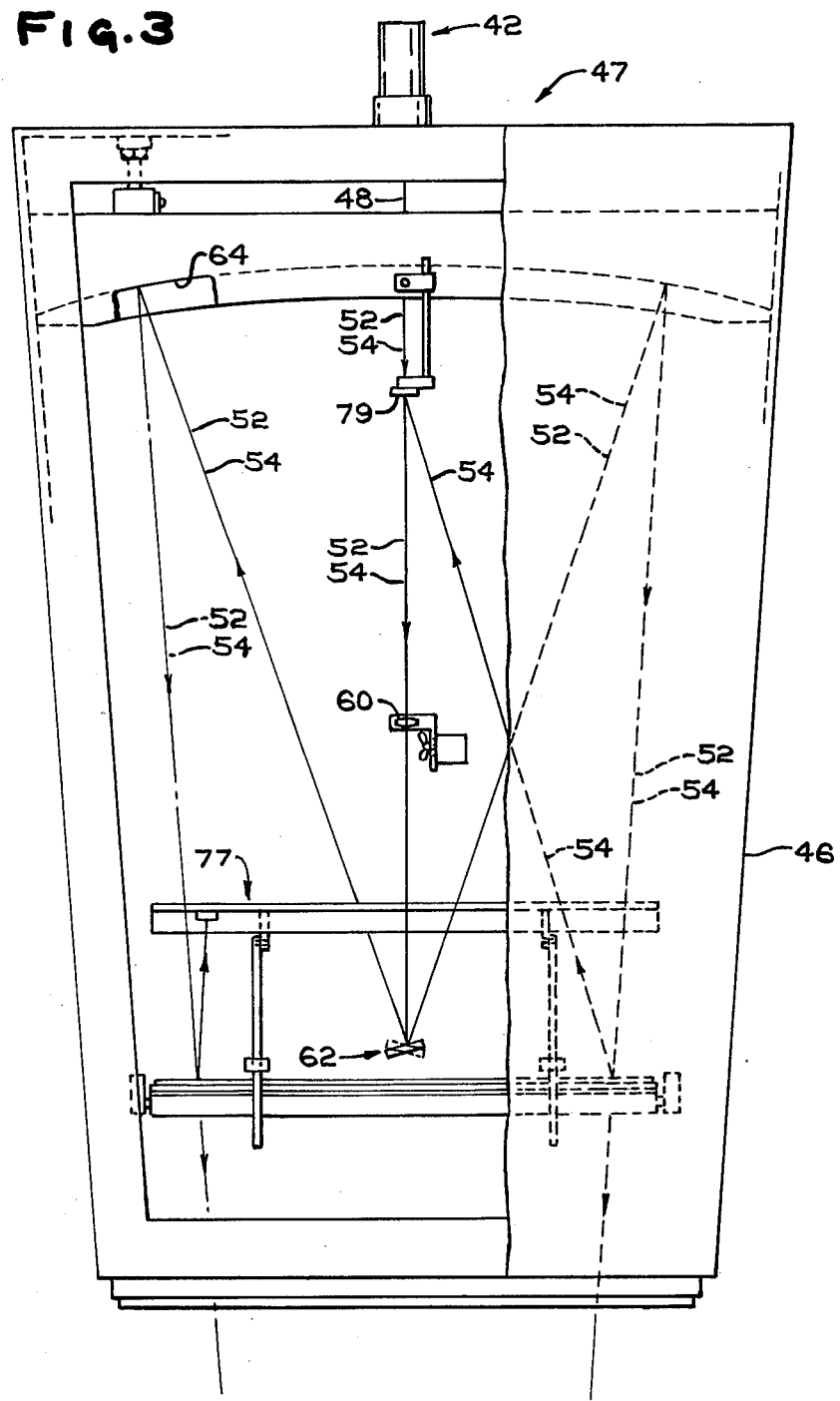

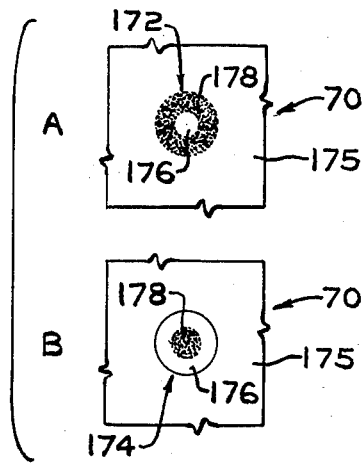
Fig.13
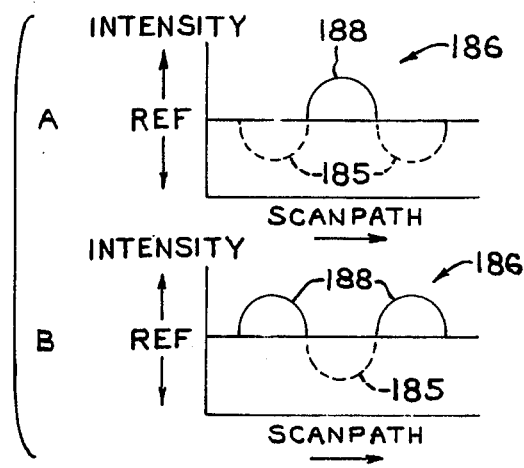
Fig.15
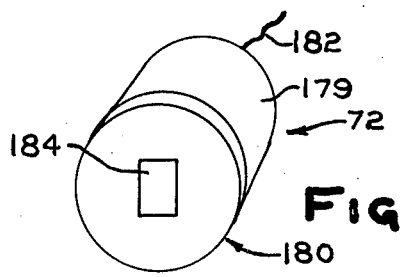
Fig.14
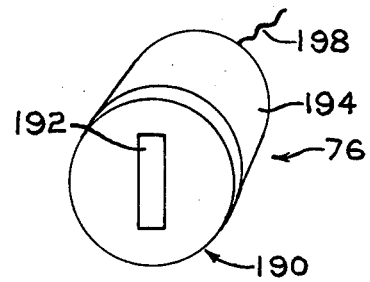
Fig.16
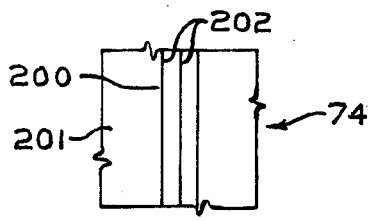
Fig.17
Fig.18
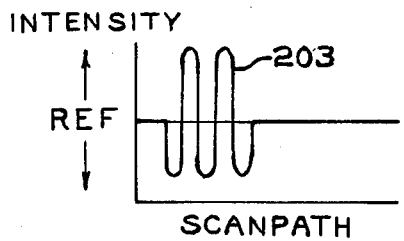
Fig.19
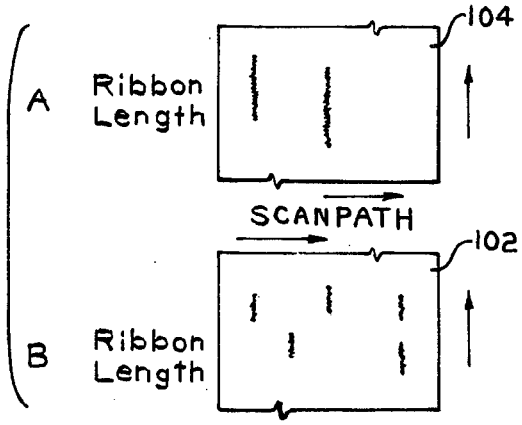

METHOD OF AND APPARATUS FOR LOCATING B TYPE AND POINT TYPE DEFECTS IN A GLASS RIBBON

BACKGROUND OF THE INVENTION

1. Field of the Invention

This invention relates to a method of and apparatus for inspecting a glass ribbon for B type and point type defects and locating their position in the glass ribbon.

2. Description of the Prior Art

In methods of making glass by the known float process, plate process or sheet process, defects may be produced in the glass which render the glass optically imperfect. Among the optical imperfections that may be produced in these processes is distortion resulting from (1) variations in glass composition, i.e., B type defects known as strings, striae and ream, and (2) pits or mounds in the surface of the glass or inclusions in the glass, i.e., point type defects.

Glass manufacturers attempt to categorize various grades of glass for various purposes. For example, highest quality mirror glass has optical requirements far in excess of those necessary for commercial glass. Further, by knowing the type of defects in the glass, selective changes can be made in the glassmaking process to eliminate or minimize the occurrence of the defects in the glass.

Taught in U.S. Pat. Nos. 3,202,043; 3,609,380; 3,737,665; 3,578,869; 3,659,950; 3,871,773; 3,688,235 and 3,917,414 are methods of and apparatuses for inspecting a web or strand material.

In U.S. Pat. Nos. 3,871,773 and 3,609,380 a scanning beam of light is moved across a moving glass ribbon. The scanning beam is transmitted through the glass ribbon incident on a detector. Variations in the signals from the detector indicate the presence of a defect. Further, U.S. Pat. No. 3,871,773 teaches that the movement of a scanning beam can be monitored during scanning to locate the position of the defect in the glass ribbon.

Although the inspection apparatuses taught in U.S. Pat. Nos. 3,871,773 and 3,609,380 are suitable for inspecting a glass ribbon for defects, there are limitations. Using a single detector does not have sufficient sensitivity to distinguish between all ranges of B type and point type defects. For example, if the detector is adjusted to sense B type defects, the sensitivity to point type defects decreases. This is because detectors used to sense B type defects analyze a longer portion of the scanning beam than the detectors used to sense B type defects.

In U.S. Pat. Nos. 3,659,950; 3,917,414; 3,578,869; 3,737,665 and 3,688,235 there are taught methods of inspecting a web material for a single parameter, e.g., thickness, circular dimension or catagorizing a defect, i.e., distinguishing between large and small discontinuities in a glass ribbon.

Although the teachings of the above-mentioned patents are acceptable for their specific use of inspecting a single parameter or catagorizing the size of a single defect, they are not capable of distinguishing between different type defects especially when the defects are point type defects and B type defects.

In U.S. Pat. No. 3,202,043 there is taught inspection of a glass ribbon for point type and D type defects. In general, a converging scanning beam of light is transmitted through a glass ribbon incident on a spatial filter, i.e., a glass plate having a mirrored portion positioned at a focal point. B type defects deflect the scanning beam to pass through the unreflected portion of the filter onto a detector. The teachings of U.S. Pat. No. 3,202,043 are acceptable for determining point type and B type defects but has limitations. The spatial filter is not acceptable for use in distinguishing between B type and point type defects because B type defects like point type defects do not change the path of the scanning beam sufficiently so as to separate B type and point type defects. Further a diverging scanning beam is more sensitive to point type defects than a converging scanning beam.

It would be advantageous therefore to provide a method of and apparatus for inspecting a glass ribbon for point type and B type defects and for locating their position in the glass ribbon.

SUMMARY OF THE INVENTION

This invention relates to an improved method of inspecting a glass, e.g., a sheet or glass ribbon for point type or B type defects. In general, a beam of light is directed toward the glass ribbon to pass the beam of light therethrough as a transmitted beam of light while the beam of light and the glass ribbon are displaced relative to one another to pass the light beam through the glass ribbon along a scan path. The improvement includes splitting the transmitted light beam into a first scanning light beam and into a second scanning light beam. The intensity variations (1) of the first scanning light beam caused by B type defects is sensed while the intensity variations caused by point type defects is minimized and (2) of the second scanning light beam caused by point type defects is sensed while the intensity variations caused by B type defects is minimized.

This invention also relates to an improved apparatus for practicing the inspection method. The apparatus includes facilities for generating a light beam and facilities for displacing the light beam and glass ribbon relative to one another to displace the light beam through the ribbon as a transmitted light beam. The improvement includes facilities for splitting the transmitted light beam into a first scanning beam and a second scanning beam. First sensing facilities sense intensity variations of the first scanning light beam caused by B type defects while minimizing intensity variations caused by point type defects. Second sensing facilities sense the intensity variations of the second light beam caused by point type defects while minimizing intensity variations caused by B type defects.

BRIEF DESCRIPTION OF THE DRAWINGS

FIG. 1 is a pictorial view of an optical system that may be used in the practice of the invention;

FIG. 2 is an elevated side view showing a pair of beam generators with a one of the beam generators having portions cut away to illustrate subassemblies of the beam generators;

FIG. 3 is an elevated front view of a beam generator having portions removed for purposes of clarity;

FIG. 13 is a representative illustration of the scanning beam at the surface of a detector showing point type defects;

FIG. 14 is an isometric view of the detector used in the practice of the invention to sense point type defects;

FIG. 15 is a graphic illustration of the output signal of the detector of FIG. 14 sensing defects corresponding to the defects shown in FIG. 13;

FIG. 16 is an isometric view of a detector used in the practice of the invention to sense B type defects;

FIG. 17 is a representative illustration of the scanning beam at the surface of the detector shown in FIG. 16;

FIG. 18 is a graphic illustration of the outut signal of the detector of FIG. 16 sensing the defect illustrated in FIG. 17; and FIG. 19 is a representative illustration of strip charts, one strip chart showing the presence of B type defects (19A) and the other strip chart showing the presence of point type defects (19B) and their position on the glass ribbon.

DESCRIPTION OF THE INVENTION

Figure 5:
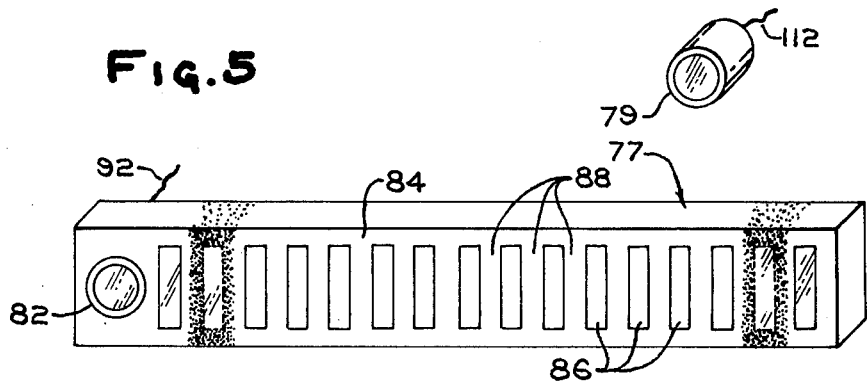
FIG. 5 is an illustrative view of a fresnell lens used in the practice of the invention to locate the position of the scanning beam along the scan path.

This invention relates to a method of and apparatus for simultaneously determining B type and point type defects in a glass ribbon or glass sheet and the position of the defect in the glass ribbon.

B type defects as the term is used herein are defects that exist within the body of the glass and result from incomplete blending of the various batch ingredients during the glass melting and fining operations and extend generally in the direction of glass draw. These defects are known in glassmaking art as strings, striae, and ream.

Point type defects as the term is used herein are those which may be within the glass, i.e., of the inclusion type, or may be present at the surface of the glass. Inclusion type defects are known in the glassmaking art but not limited thereto as stones, boils, blisters and seeds. Surface point type defects are known in the glassmaking art but not limited thereto as concave and convex portions in the glass surface as well as tin dripping on top of the glass surface.

Shown in FIG. 1 is a pictorial view of an optical system 40 of the type taught in commonly assigned U.S. Pat. No. 3,871,773 that may be used in the practice of the invention. The teachings of the above-identified patent are hereby incorporated by reference.

The optical system 40 including a light source 42, a mirror system 44 and position determining facilities 45 is advantageously mounted in a housing 46 of a scan beam generator 47 as shown in FIGS. 2 and 3.

With reference to FIGS. 1, 2 and 3, the light source 42, such as a laser, directs a beam of light 48 toward a beam splitter 50 of the mirror system 44 to split the beam of light 48 into a scanning beam 52 and a positioning beam 54. The scanning beam 52 is transmitted through a diverging lens 56 and the positioning beam 54 toward a first stationary mirror 58.

The scanning beam 52 passes through the diverging lens 56 and then through a converging lens 60 and is incident on the surface of an oscillating directional mirror 62 positioned at a first focal point of a concave or elliptical reflecting surface or mirror 64. The focal point and distance of the diverging lens 56 and the converging lens 60 are selected so that the scanning beam 52 is incident on the concave mirror 64 generally as a point.

The scanning beam 52 is reflected from the concave reflecting surface 64 through a glass ribbon 66 along a scan path 67 (see FIG. 4) transverse to the movement of the glass ribbon 66. The scanning beam 52 transmitted through the glass sheet is incident on the surface of beam splitter 68.

Figure 4:
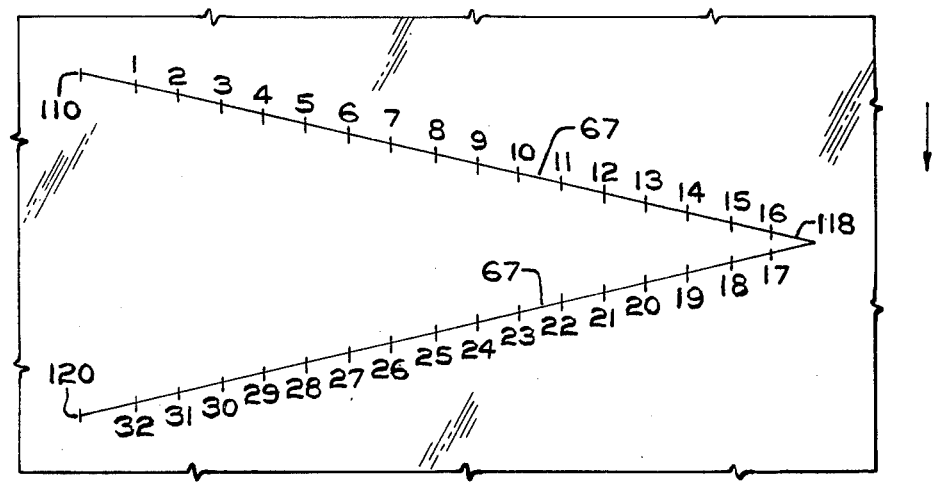
FIG. 4 is a section of a glass ribbon illustrating a scan path using the optical system shown in FIG. 1.
Figure 6:
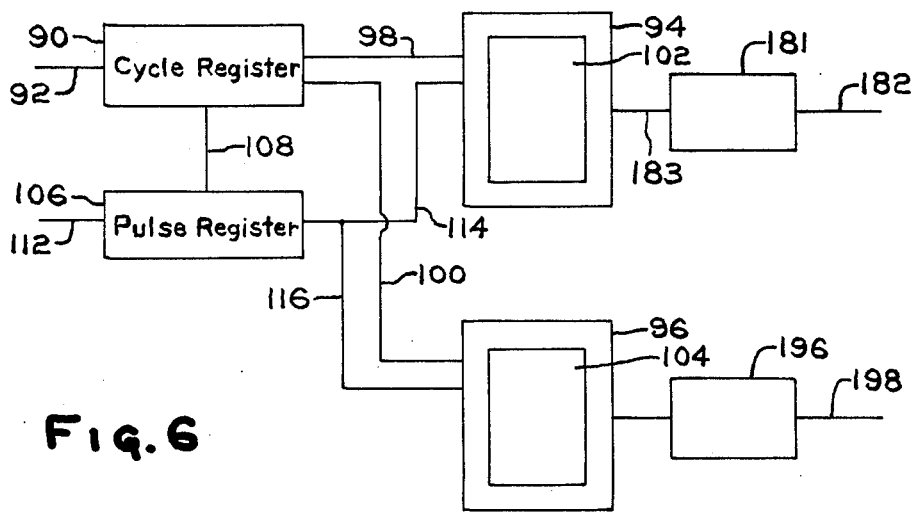
FIG. 6 is a block diagram of an electrical system that may be used in the practice of the invention to record the presence and position of B type and point type defects in a glass ribbon.

Referring to FIG. 4, the length of the scan path 67 is controlled by (1) the distance of the glass ribbon 66 from the concave reflecting surface 64, (2) the arc of the concave reflecting surface 64, and (3) the arc subtended by the oscillating directional mirror 62. The scanning beam reflected from the concave mirror diverges, therefore as the distance between the concave mirror and glass ribbon increases, the width of the scan path 67 increases and visa versa.

As shown in FIG. 1, the beam splitter 68 splits the scanning beam 52 into a first split scanning beam 70 incident on detector 72 positioned at the focal point of the concave reflecting surface 64 and into a second split scanning beam 74 incident on detector 76. The distance of the detector 76 from the beam splitter 68 is approximately equal to the distance of the detector 72 from the beam splitter 68 so that the detector 76 is considered positioned at the second focal point of the concave reflecting surface 64.

The beam splitter 68 and detectors 72 and 76 incorporating features of the invention will be discussed in more detail below.

With reference to FIGS. 1, 2 and 3, the positioning beam 54 is reflected from the first stationary mirror 58 and is incident on the oscillating directional mirror 62. The positioning beam 54 is reflected from the oscillating directional mirror 62 along the reflecting surface 64 in synchronous movement with the scanning beam 52.

The positioning beam 54 is reflected from the reflecting surface 64 toward a fresnell lens 77 and a light responsive device 79 (shown better in FIG. 5) by way of a second stationary mirror 80. The light responsive device 79 is positioned at the focal point of the fresnell lens 77 so that the positioning beam passing through the fresnell lens is incident on the light responsive device 79.

As shown in FIG. 5, the fresnell lens 77 is provided with a photocell 82 and the surface of the fresnell lens is selectively coated with light-absorbing paint 84 to provide light-passing areas 86 through which the positioning beam passes to actuate the light responsive device 79 and light absorbing areas 88 to block the positioning beam from the light responsive device 79, to determine the position of the scanning beam along the scan path 67.

With reference to FIG. 3, rotating the oscillating directional mirror 62 in a clockwise direction synchronously displaces the scanning beam 52 and positioning beam 54 from left to right across the reflecting surface 64 and rotating the oscillating directional mirror 62 in a counter clockwise direction, synchronously displaces the scanning beam and positioning beam from right to left across the reflecting surface 64, as viewed in FIG. 3.

With reference to FIGS. 3, 4, 5 and 6 when the scanning beam 52 is at the initial position on the reflecting surface 64, i.e., at the extreme left end of the concave reflecting mirror 64 as shown in FIG. 3, the positioning beam 54 is incident on the photocell 82. A pulse from the photocell 82 is forwarded to a cycle register 90 by way of cable 92 to increase the number in the cycle register 90 by one and forward a pulse to strip chart recorders 94 and 96 by way of cables 98 and 100 to appropriately mark charts 102 and 104, respectively, to indicate the position of the scanning beam along the length of the glass ribbon. The cycle register 90 simultaneously forwards a signal to pulse recorder 106 by way of cable 108 to clear the pulse recorder 106.

Controlling the speed of the glass ribbon and the speed of the scanning beam, the length of the glass ribbon scanned for each cycle can be determined. Recording the scan cycle number and knowing the length of the ribbon covered during a scan cycle the position of the scanning beam along the glass draw can be determined.

As the scanning and positioning beams are synchronously displaced along the reflecting surface 64 by rotating the oscillating directional mirror 62 in a clockwise direction, the positioning beam 54 is moved from left to right as viewed in FIG. 3, from the photocell 82 onto an adjacent light-absorbing area 86 of the fresnell lens 77 and then to one of the light-passing areas 86 (see FIG. 5). Simultaneously with the movement of the positioning beam across the surface of the fresnell lens, the scanning beam moves from the initial position on the concave reflecting surface 64 and from the initial position 110 on the scan path 67 to the right to start scanning the glass ribbon 14 for defects along the scan path 67 as shown in FIG. 4. The intensity of the scanning beam 54 sensed by the detectors 72 and 76 is recorded on the charts 102 and 104, respectively, in a manner to be described below.

Each time the positioning beam moves past a light-passing area 86 and a light absorbing area 88 a signal is forwarded from the light responsive device 79 to the pulse register 106 by way of cable 112. The pulse register 106 increases by one and forwards a signal to the strip chart recorders 94 and 96 by way of cables 114 and 116 to mark the charts 102 and 104, respectively. The pulse count and associated mark on the charts 102 and 104 indicate the position of the scanning beam along the scan path 67.

When the scanning beam and positioning beam are at mid-cycle position, i.e., at the right of the concave reflecting mirror as viewed in FIG. 3, the directional mirror rotates in counter clockwise direction. The positioning beam and the scanning beam move from right to left on the concave reflecting surface as viewed in FIG. 3 toward the initial position. The scanning beam is now displaced from mid-cycle scanning position 118 on the scan path 67 and the positioning beam is displaced along the fresnell lens 70 from right to left as viewed in FIG. 5. As before, each time the positioning beam moves past a light-passing area 86, the positioning beam is incident on the light responsive device 79 to forward a signal to the pulse register 106 to increase the number therein while recording the number on the charts 102 and 104.

At the end of a scan cycle, the positioning beam and scanning beams are at the left side of the concave reflecting mirror 64. Further the positioning beam is incident on the photocell 82 and the scanning beam is at the end of the scan path or beginning of the next scan path designated by the number 120. The photocell 82 forwards a pulse to the cycle register 90 (1) to record a digit indicating the start of the next scanning cycle, (2) clear the pulse register 106 and (3) mark the charts 102 and 104 to indicate the start of the next scan cycle. By repeating the above procedure, the charts 102 and 104 will display a scanning profile of the glass ribbon. The width of the light-blocking areas 88 of the fresnell lens 77 (see FIG. 5) should be greater than the diameter of the positioning beam incident on the fresnell lens, thereby blocking the positioning beam from the light responsive device to allow the pulse register 106 to reset.

Figure 8:
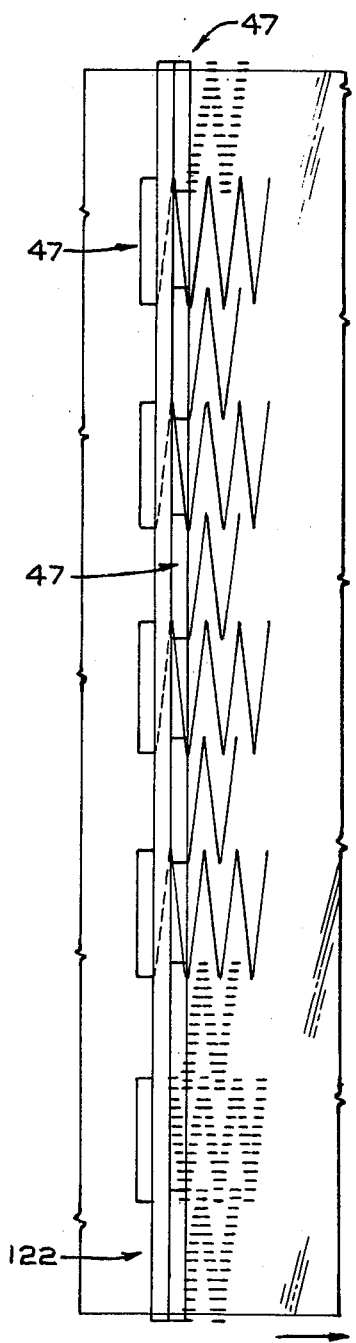
FIG. 8 is an illustration showing the relationship the beam generates to the glass ribbon as well as scan paths on the glass ribbon.
Figure 7:
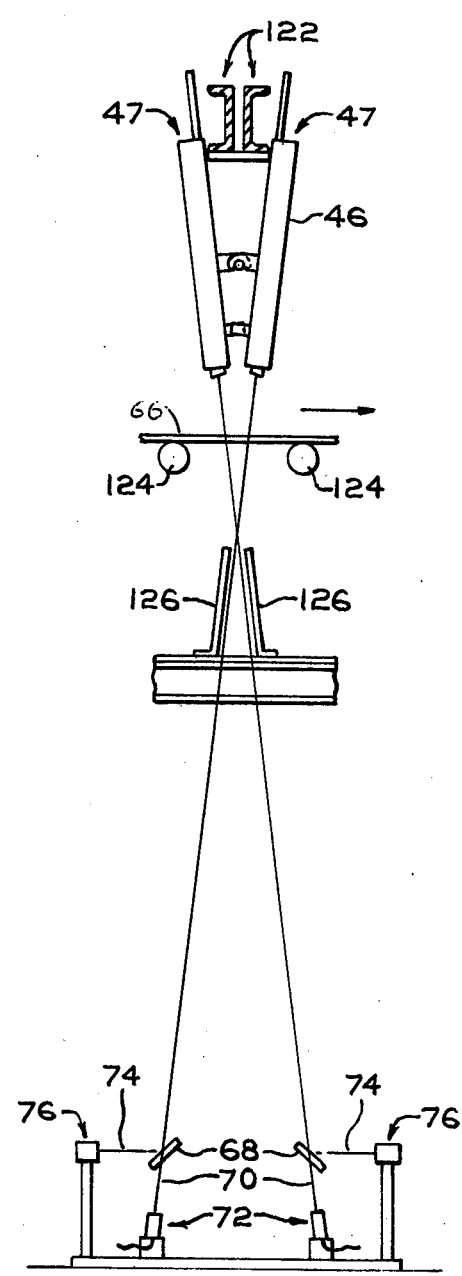
FIG. 7 is an elevated side view showing the inspection of a glass ribbon in accordance to the teachings of the invention.

Referring to FIG. 7, there is shown a side view of a pair of scan beam generators 47 mounted above th glass ribbon 66 by way of support member 122. The glass ribbon 66 is moved from left to right, as viewed in FIG. 7, on conveyor rollers 124. The glass ribbon 66 is completely scanned for defects by mounting a series of beam generators 47 on one side of the supports 122 a predetermined distance apart and another series of beam generators on the other side of the support members 122 a predetermined distance apart with one series of beam generators offset from the other series of beam generators as shown in FIG. 8. Each of the beam generators scan a predetermined lateral portion of the glass ribbon to scan the width of the glass ribbon for defects.

To prevent particles from falling onto the surface of the photo detectors 72 and 76, a pair of plates 126 are mounted beneath the conveyor rollers 124 and angled toward each other as shown in FIG. 7. The detectors 72 and 76 are offset from a center line between the plates 126. With this arrangement, particles and broken glass falling between the plates 126 will not fall on the photo detectors 72 and 76.

Although not required to practice the invention but recommended to inspect 100 percent of the glass ribbon 66 for defects, the speed of the oscillating directional mirror, the speed of the glass ribbon and the diameter of the scanning beam incident on the surface of the glass ribbon should be selected such that the distance between the start of the scan path 110 and the end of the scan path 120, i.e., the start of the next scan path (see FIG. 4) is less than the diameter of the scanning beam incident on the surface of the glass ribbon. In this manner, contiguous lateral portions of the glass ribbon can be inspected.

As will be appreciated, the invention is not limited to the optical system 40 described and that it was presented for purposes of illustrating one type of optical system that may be used in the practice of the invention.

Figure 10:
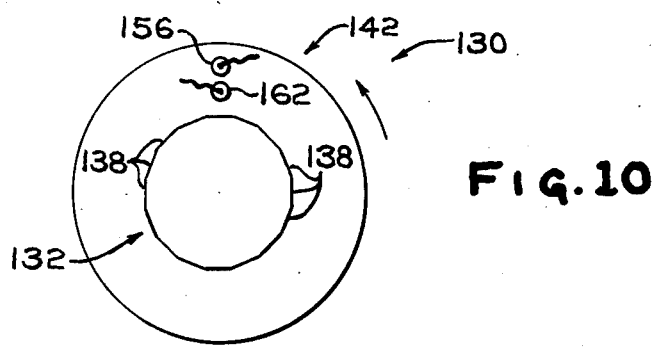
FIG. 10 is a frontal view of the device shown in FIG. 9.
Figure 9:
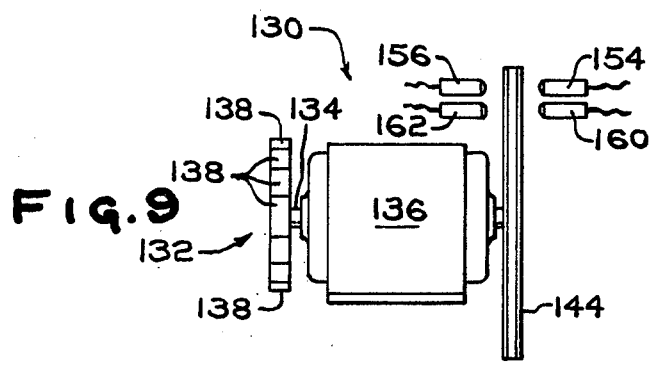
FIG. 9 is a side view of a scanning and positioning device that may be used in the practice of the invention.
Figure 11:
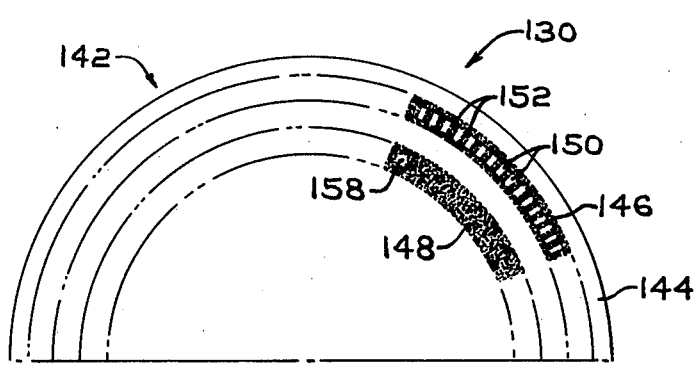
FIG. 11 is a rear view of the device shown in FIG. 9.

Shown in FIGS. 9, 10 and 11 is a beam displacing and determining device 130 that may be used in the practice of the invention. The beam displacing device 130 includes a prismatic mirror 132 mounted on the end of shaft 134 of motor 136. The prismatic mirror 132 is of the type taught in commonly assigned U.S. Pat. No. 3,609,380 and the teachings therein are hereby incorporated by reference.

Mirrored surfaces 138 of the prismatic mirror 132 rotate through the focal point of the concave reflective mirror 64 to displace the scanning beam across the surface of the concave mirror 64.

Figure 12:
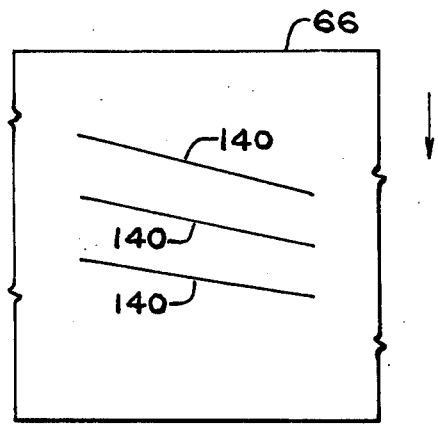
FIG. 12 is the scan path of a scanning light beam on a glass sheet generated using the device shown in FIGS. 9-11.

Shown in FIG. 12 are scan paths 140 of the scanning beam incident on the glass sheet 66. Each mirror generates a scan path that is a straight line transverse to the path of the glass ribbon and parallel to one another.

The beam determining portion of the device 130 includes a light passing disc 142 mounted on the motor shaft 134 so that the disc 142 and the prismatic mirror 132 are rotated together.

As shown in FIG. 11, disc surface 144 is provided with an outer circular band 146 and an inner circular band 148 each having its axis coincident with the rotating axis of the disc 142. The outer circular band 146 has a plurality of series of light passing areas 150 and light absorbing areas 152. One of the series of the light passing areas 150 corresponds to a one of the mirrored surfaces 138 of the prismatic mirror 132. A stationary light source 154 directs a beam of light onto the path of the circular band 146 and is incident on a light responsive device 156 when a light passing area 150 is moved past the light source 154 to determine the position of the scanning beam on the scan path 140 in a similar manner as the position of the scanning beam was determined on the scan path 67 using the fresnell lens 77 and light responsive device 79 shown in FIGS. 4 and 5.

The start of the scan cycle, i.e., when the scanning beam is at a corner of a mirrored surface 138 of the prismatic mirror 132 is indicated by providing a light passing area 158 on a light absorbing inner circular band 148. A light beam from stationary ligth source 160 aligned with light responsive device 162. When a light passing area 158 moves past the light source 160, the scanning beam is at a side of a mirrored surface 138, i.e., the start of a scan cycle and the beam from the light source 160 is incident on the light responsive device 162. The light passing areas 158, the light source 160 and light responsive device 162 operate in a similar manner as the photo cell 82 and the positioning beam 54 discussed for FIG. 5.

The discussion will now be directed to the detectors 72 and 76 for sensing B type and point type defects. In the following discussion, detector 72 will be used for sensing point type defects, and the detector 76 for sensing B type defects, however the invention is not limited thereto.

Point type defects such as inclusions in the glass and concave and convex portions on the glass surface have a lens effect on the scanning beam 52 that converges and diverges the light beams. Shown in FIG. 13 are illustrated typical light patterns 172 and 174 at the surface of the detector 72 of a scanning beam passing over a point type defect. The background 175 of the scanning beam is the referenced intensity. Area 176 has an intensity greater than the reference intensity and dark area 178 has an intensity less than the intensity of the background 175 and area 176 due to the lens effect of the point type defect. When the scanning beam at the surface of the detector 72 has only reference intensity and dark areas, the point type defect does not have a lens but a blocking effect indicating dirt or tin dripping on the glass ribbon surface.

Shown in FIG. 14, the detector 72 includes a photocell 179 having a plate 180 mounted over the photo cell surface. The photocell 179 is connected to electrical system 181 by way of cable 182 to convert the signal from the photocell indicating an intensity other than the referenced intensity. These pulses are forwarded to recorder 94 by way of cable 183 to mark the chart 102.

The plate 180 has a slit 184 sized to minimize the background intensity 175 of the scanning beam. In other words, the length of the slit is slightly larger than the expected maximum diameter of the light are 176 of FIG. 13B or dark area 178 of FIG. 13A so that the photo detector 179 can sense intensity variations of the scanning beam at the plate 180.

The width of the slit is selected to resolve the light intensity variations of the scanning beam as it moves across the slit 184. For example, if the slit is too wide, the light and dark areas would be integrated and the signal lost.

Referring now to FIGS. 13, 14 and 15 as the background 175 of the scanning beam in FIG. 13A passes over the slit 184, the signal of the detector is at its reference value. As the dark area 178 passes over the slit 184, the intensity of the scanning beam decreases and the output signal of the detector 179 is less than the reference signal as shown by dotted portion 185 of the curve 186 in FIG. 15A. When the light area 176 passes over the slit 184, the intensity of the scanning beam is greater than the reference intensity and the output signal of the detector 179 is greater than the reference intensity as shown by solid portion 188 of the curve 186.

To distinguish between dirt on the glass and point type defects, the electrical system 181 is adjusted in any conventional manner to pass only positive signals. Dirt on the glass prevents light from passing through the glass and decreases the intensity of that portion of the beam passing over the dirt. Passing only positioned signals, the dirt does not appear as a point type defect. In this instance the solid portion 188 of the curve 186 of FIGS. 15A and 15B is acted on by the electrical system 181. The amplitude of the output signal of the detector 179 is a function of the lens effect of the point type defect. In general, the larger the defect in the glass, the higher the output signal of the detector 179.

The invention also contemplates catagorizing point type defects by size. This may be accomplished by adjusting the electrical system 181 in any conventional manner to pass output signals of the detector 179 in a preselected range. Further practicing the invention at preselected positions along the ribbon path, the point type defects can be catagorized as to their size.

With reference to FIG. 16, there is shown the detector 76 for determining B type defects. As was mentioned above, B type defects are elongated in the direction of the draw and like point type defects increase and decrease the intensity of the scanning beam. The detector 76 includes a plate 190 having a slit 192 mounted over a photocell 194 electrically connected to electrical system 196 by cable 198. The slit 192 of the plate 190 is aligned with the direction of the glass ribbon movement.

The length of the slit 192 is selected so that point type defects do not generate a signal of sufficient magnitude to actuate the electrical system 196 to mark the chart 104. This may be accomplished in the following manner. With reference to FIG. 17, there is illustrated a typical B type defect pattern of the scanning beam incident on the plate 190 of the detector 76. Portion 200 of the scanning beam 74 is darker than the background intensity 201 and portion 202 is lighter than the background intensity 201 and dark portions 200.

The B type defect is elongated (see FIG. 17) whereas the point type defect is generally circular (see FIG. 13). To distinguish between B type and point type defects, the slit 192 of the detector 76 has a length greater than the slit 184 of the point type detector 72 such that a point type defect on the B type detector 76 has an output signal indicating low intensity. In other words the diameter of the dark area 178 of FIG. 13A and the light area 176 of FIG. 13B is much smaller than the length of the slit 192 of the detector 76.

The amplitude of the detector signal is a function of the B type defect, e.g., ream grade or severity. As the ream grade or severity increases, the amplitude increases and vise versa.

As can now be appreciated, the invention may be practiced to catagorize B type defects as to grade or severity. This may be accomplished by practicing the invention at predetermined positions along the glass ribbon path. The electrical system 196 at each of the predetermined positions is adjusted to pass a predetermined range of B type defects.

Shown in FIG. 19 is the chart 102 for plotting B type defects and chart 104 for plotting point type defects. B type defects are elongated in the direction of ribbon drawn and are shown as a series of dots along the ribbon length. Point type defects are normally in a discrete area and have a shorter duration along the ribbon length.

Practicing the instant invention, a glass ribbon or sheet of glass can be inspected for B type and point type defects, distinguished between B type and point type defects and locate the position of the defect on the glass ribbon.

As can be appreciated, variations in the practice of the invention can be made without deviations from the scope of the invention. For example, point type defects and B type defects can be graded. This may be accomplished by having standards, i.e., glass plates having point type defects of known size and B type defects of known grade or severity. The standards are placed in the path of the scanning beam and the electrical systems 181 and 196 are adjusted to pass only detector signals of a predetermined value range. In this manner, only point type defects and B type defects of a known grade will be marked on the charts 102 and 104.

DETAILED DESCRIPTION

The invention is practiced to scan a glass ribbon for point type and B type defects. As can be appreciated by those skilled in the art, the invention is not limited thereto.

Referring to FIGS. 7 and 8, two rows of scan beam generators 47 are advantageously mounted to each side of a support member 122 such that a scanning beam has an angle of incidence of 6° or 7° to a line normal to the surface of glass ribbon 66 to reflect the portion of the scanning beam reflected from the surface of the glass ribbon away from the beam generators. In one row, there are six beam generators spaced about 14 inches (0.31 meter) apart and offset from five scan beam generators in the other row spaced about 14 inches (0.31 meter) apart. Each of the generators has a concave elliptical mirror (see FIG. 3) about 24 inches (0.6 meter) in length having a first focal point of 29¼ inches (0.67 meter) and a second focal point of 192¼ inches (4.8 meters). The concave mirror is spaced about 50½ inches (1.21 meters) from the glass ribbon 66 to scan about a 16 inch (0.32 meter) lateral zone of the glass ribbon. Providing eleven generators having capabilities of scanning about a 16 inch (0.32 meter) zone, the width of a glass ribbon 160 inches (4.0 meters) wide can be scanned 100 percent for defects across its width.

Referring to FIGS. 1 and 2, a light beam 48 from a multimode helium neon laser 42 passes through a beam splitter 50. The light beam 48 is split into (1) positioning beam 54 which is incident on a first stationary mirror 58 and on mirror of an oscillational directional mirror 62, (2) into scanning beam 52 which is transmitted through a diverging lens 56, a converging lens 60 and is incident on the oscillating directional mirror 62. The oscillating directional mirror 62 is poistioned at the first focal point of the concave reflecting surface 64. The diverging lens has approximately a 0.4 inch (10 millimeter) diameter and a focal point of 0.8 inch (20 millimeters); and the converging lens has approximately a 1.2 inch (30 millimeter) diameter and 10 inch (250 millimeter) focal length. The diverging lens and converging lens are spaced 25½ inches (0.6 meter) and 11½ inches (0.3 meter), respectively, from the oscillating directional mirror 64.

Referring to FIG. 3, the oscillating directional mirror 62 is rotated counter clockwise as viewed in FIG. 3 to synchronously displace the scanning beam and positioning beam from left to right across the concave reflecting surface 64 as viewed in FIG. 3. The scanning beam is transmitted through the glass ribbon and is incident on a beam splitter 68 spaced 185 inches (4.6 meters) from the reflecting surface. The scanning beam is split (1) into a first split scanning beam 70 incident on detector 72 positioned 7¼ inches (18 centimeters) from the beam splitter 68 or 192¼ inches (4.8 meters) from the concave reflecting mirror, i.e., at the second focal point of the mirror and (2) into a second split scanning beam 74 incident on photo detector 76 positioned about 7¼ inches (18 centimeters) from the beam splitter 68.

With reference to FIGS. 14 and 16, each of the detectors 72 and 74 include a photo detector 179 and 194, respectively, of the type sold by Dumont photo multiplier 6292. The detector 72 has plate 180 having a slit ½ inch (1.27 centimeters) long and ⅛ inch (0.64 centimeter) wide to sense point type defects in the glass. The detector 76 has a plate 190 having a slit 192, 2 inches (5.08 centimeters) long and ⅛ inch (0.64 centimeter) wide for sensing B type defects in the glass ribbon.

The scanning beam at the surface of the glass ribbon covers a 2 inch (5.08 centimeters) diameter circular poriton. The speed of the oscillating mirror 62 is about 15 cycles per second and the speed of the ribbon is about 700 inches per minute (5 meters per minute). As the scanning beam is displaced along a scan path 67 (see FIG. 4), the distance between the start of the scan path 110 and end of the scan path 120 on the glass ribbon is 2 inches (5.08 centimeters). By providing (1) a beam at the surface of the glass ribbon having a 2 inch (5.08 centimeters) diameter and (2) the distance between scanning paths of 2 inches (5.08 centimeters) the entire length of the glass ribbon may be inspected for defects.

Referring back to FIGS. 2 and 3, the positioning beam is reflected from the concave reflecting surface 64 and is incident on a second stationary mirror 74 which reflects the positioning beam toward a fresnell lens 77 and a light responsive device 77 mounted at the focal point of the fresnell lens.

Referring to FIGS. 4 and 5, when the scanning beam 52 is at the initial position, i.e., the extreme left-hand position of the concave mirror 46 (see FIG. 3), the positioning beam is incident on a photocell 85 of the fresnell lens 77 (see FIG. 5). The photocell 85 forwards a pulse to cycle register 90 to register the number of scanning cycle on the charts 102 and 104 and to set the pulse register 106 to zero (see FIG. 6). As the glass ribbon moves from left to right as viewed in FIG. 7, the mirror rotates clockwise as viewed in FIG. 3 to synchronously displace the scanning beam and positioning beam from left to right across the concave reflecting surface 64. The scanning beam is displaced along the first half of the scan path 67 between 110 and 118 as the positioning beam is displaced from left to right across the coated surface of the fresnell lens as viewed in FIG. 5. As the positioning beam 54 is successively displaced over each one of 16 light-absorbing areas 84, the positioning beam actuates the light responsive device which forwards a signal by way of cable 112 to the pulse register 106 (see FIG. 6). For each signal received by the pulse register 106, the number registered therein is increased by one and the new number forwarded to the strip chart recorders 94 and 96 and recorded on charts 102 and 104, respectively.

With reference to FIG. 14, plate 180 of detector 72 having a slit 184 having a length of ½ inch (1.27 centimeters) and a width of ¼ inch (0.64 centimeter) is positioned over the photo detector 179. A piece of glass having point type defects of a diameter of greater than about 0.006 inch (0.015 centimeter) is scanned by the scanning beam. A signal from the detector 72 is forwarded to electrical system 181 by way of cable 182. The electrical system 181 is adjusted to pass positive signal of the detector 72 in response to the point type defects on the sample. The electrical system converts the signal to a pulse that is forwarded to recorder 94 for marking chart 102 with a dot (see FIG. 19B).

Referring now to FIG. 16, plate 190 of detector 76 having a slit 2 inches (5.08 centimeters) in length and ¼ inch (0.64 centimeter) wide is positioned over photo detector 194. A piece of glass having grade 4 ream is scanned by the scanning beam. A signal from the detector 76 is forwarded to electrical system 196 by way of cable 198. The electrical system 196 is adjusted to pass the signal of the detector 76 in response to grade 4 or higher ream in the glass sample. The electrical system 196 converts the signal to a pulse that is forwarded to recorder 96 for marking chart 104 with a dot (see FIG. 19A).

The dots for B type defects having a longer length along the glass ribbon than the dots for point type defects as shown on the charts 104 and 102, respectively, in FIG. 19.

The apparatus is now ready for inspection of the glass ribbon 66. The glass ribbon 66 is moved from left to right as viewed in FIG. 7 by conveyor rollers 124 as the scanning beam from the scan beam generator scans the glass transverse to its path for defects.

As the intensity variations of the scanning beam 70 and 74 is sensed by the detector 72 and 76, respectively, and recorded on the charts 104 and 102, respectively, the positioning beam moves across the fresnell lens 77 (see FIG. 5) to record the position of the scanning beam along the scan path and the length of the ribbon. For example, when the positioning beam 54 is incident on the light response device 82 of the fresnell lens 77, a pulse is forwarded to cycle register 90. For each pulse of the photocell 86 the cycle register 95 forwards a signal to the strip chart recorders 94 and 96 to mark the charts 102 and 104 to indicate the scan cycle and the following intensity readings pertaining thereto. Each pulse forwarded from the light responsive device 79 shown in FIG. 5 to the pulse register 97 shown in FIG. 6 increases the count in the register 97 and forwards a signal to the strip chart recorders 94 and 96 to mark the charts 102 and 104 to indicate the portion of the scan path that the intensity recorded pertains.

At the end of the first half of the scanning cycle, the pulse counter register has registered 16 counts, one count for each light-passing area which corresponds to predetermined 1 inch (2.54 centimeters) length of the scan path. At the start of the second half of the scan cycle, the directional oscillating mirror is rotated counter clockwise as viewed in FIG. 3 to displace the scanning beam and positioning beam from right to left across the concave reflecting surface 64. The scanning beam is moved along the second half of the scan cycle and the positioning beam is moved from right to left across the fresnell lens 77 as viewed in FIG. 5.

At the end of the second half of the scanning cycle, the scanning beam is at the initial position on the concave mirror (see FIG. 3) and the positioning beam is incident on the light response device 82 (see FIG. 5). A signal from the device 82 is forwarded to the cycle register 90 to indicate the start and number of the next scanning cycle and clearing the pulse register 106. The system is now ready to scan another portion of the glass ribbon for defects. By recording the number of cycles of scan and recording intensities as a function of pulse counts, the position of defects on the ribbon can be determined as well as whether the defect is a point type or B type defect.

Referring to FIGS. 9–11 there is shown a scanning and position device that may be used in place of the oscillating mirror 62 and positioning determining facilities 45. The device 130 has a prismatic mirror 132 having 12 flat mirrored surfaces 138. The mirror 132 is mounted on shaft 134 of motor 136 and the motor positioned such that the mirrored surfaces 132 rotate through the first focal point of the concave reflective mirror 64 to reflect the scanning beam onto the concave reflecting surface 64. Shown in FIG. 12 is scan path 140 of the scanning beam along the glass surface. The scanning pattern is a plurality of parallel lines transverse to the glass travel.

Referring now to FIGS. 10 and 11, a disc 142 is mounted on the other end of the shaft 134 of the motor 136. With specific reference to FIG. 11, the surface 144 of the disc is provided with ½ inch (1.27 centimeter) wide outer circular bands 146 and ½ inch (1.27 centimeter) wide inner circular band 148 each having their center coincident with the rotating center of the disc 142. The outer band 146 has 12 groups of 16 equally spaced light passing areas 150 separated by light absorbing areas 152. The inner band 148 has 12 discrete light passing areas 158 separated by light absorbing areas 148. The light passing areas 158 are aligned with the corners of the mirrored surfaces 138. Light beams from stationary light sources 154 and 160 are directed onto the bands 146 and 148, respectively, and aligned with light responsive devices 156 and 162, respectively.

As the disc rotates the light beam from light source 156 is incident on the light detector 156. The detector 156 forwards a pulse to the pulse register 106 to indicate the position of the scanning beam along the scan path 140 in a similar manner as was discussed for the fresnell lens 77 and photocell 79 shown in FIG. 5.

When the light beam from light source 160 is incident on the light responsive device 162, a pulse is forwarded to the cycle register 90 to locate the scanning beam along the length of the ribbon as was discussed for the photocell 82 as shown in FIG. 5.

As can be appreciated, the invention is not limited to the above embodiments and the examples were presented for illustration purposes only.

What is claimed is:

1. In a method of inspecting a glass for point type and B type defects wherein the method includes the steps of directing a beam of light toward the glass to pass the beam of light through the glass as a transmitted beam of light; and displacing the beam of light and glass relative to one another to pass the beam of light through the glass along a scan path, the improvement comprising the steps of:

splitting the transmitted beam of light into a first scanning light beam and a second scanning light beam;

passing a generally rectangular portion of the first scanning light beam having a length greater that its width to (1) minimize ratio of light to dark areas of the first scanning light beam caused by point type defects and (2) maximize ratio of light to dark areas of the first scanning light beam caused by B type defects;

sensing intensity variations of the generally rectangular portion of the first scanning light beam to determine B type defects in the glass;

passing a generally rectangular portion of the second scanning light beam having a length less than the length of the rectangular portion of the first scanning light beam to (1) minimize ratio of light to dark areas of the second scanning light beam caused by B type defects and (2) maximize ratio of light to dark areas of the second scanning light beam caused by point type defects; and sensing intensity variations of the rectangular portion of the second scanning beam to determine point type defects.

2. The glass inspecting method as set forth in claim 1 further including the step of determining the location of the B type and point type defects in the glass.

3. The glass inspecting method as set forth in claim 1 wherein said step of sensing point type defects includes the steps of:

generating an electrical signal in response to intensity variations of the rectangular portion of the second scanning light beam caused by point type defects; and passing electrical signals having a predetermined value.

4. The glass inspecting method as set forth in claim 1 wherein said step of sensing intensity variations of the rectangular portion of the first scanning light beam and said step of sensing intensity variations of the rectangular portion of the second scanning light beam includes the steps of:

generating a first electrical signal in response to intensity variations of the rectangular portion of the first scanning light beam caused by B type defects and a second electrical signal in response to intensity variations of the rectangular portion of the second scanning light beam caused by point type defects; and passing predetermined values of the first and second signals to determine a predetermined size range of the B type and point type defects, respectively.

5. An apparatus for inspecting a glass for point type and B type defects wherein the apparatus is of the type having means for generating a beam of light and means for displacing the light beam and glass relative to one another to displace the light beam through the glass as a transmitted beam of light along a scan path, the improvement comprising:

means for splitting the transmitted light beam into a first scanning light beam and a second scanning light beam;

first plate having a generally rectangular-shaped slit having a length greater than the width for (1) minimizing ratio of light to dark areas of the first scanning light beam caused by point type defects and (2) maximizing ratio of light to dark areas of the first scanning light beam caused by B type defects;

first means for sensing intensity variations of the first scanning light beam passing through said first plate as a first rectangular scanning light beam to determine B type defects in the glass;

second plate having a generally rectangular-shaped slit having a length less than the length of the slit of said first plate for (1) minimizing ratio of light to dark areas of the second scanning light beam caused by B type defects and (2) maximizing ratio of light to dark areas of the second scanning light beam caused by point type defects; and second means for sensing intensity variations of the second scanning light beam passing through said second plate as a second rectangular scanning light beam to determine point type defects in the glass.

6. The glass inspecting apparatus as set forth in claim 5 wherein said splitting means is a light beam splitter.

7. The glass inspecting apparatus as set forth in claim 5 further including:

means for locating the position of the B type and point type defects in the glass.

8. The glass inspecting apparatus as set forth in claim 7 wherein the means for generating the transmitted light beam includes a rotating multi-surfaced prismatic mirror and further including:

a disc having a first circle of a plurality of discrete light passing areas, selected ones of the discrete light passing areas correspond to a selected surface of the prismatic mirror and the position of the light beam on the scan path and a second circle of discrete light passing areas, selected ones of the discrete light passing areas of the second circle correspond to the position of the light beam at the start of each scan path and position of the scan path on the glass;

means for impinging a light beam onto a discrete portion of the first and second circle;

first light responsive means aligned with the first circle;

second light responsive means aligned with the second circle; and means for synchronously rotating the disc and mirror wherein light passing through the discrete light passing areas of the first circle impinges on the first responsive means to generate a pulse to indicate the position of the beam of light on the scan path and light passing through the discrete light passing areas of the second circle impinges on the second responsive means to generate a pulse to indicate the position of the scan path on the glass.

9. The glass inspecting apparatus as set forth in claim 5 wherein said second sensing means includes:

means for generating an electrical signal in response to intensity variations of the second rectangular scanning light caused by point type defects; and means for passing electrical signals of a predetermined value.

10. The glass inspecting apparatus as set forth in claim 5 wherein said first and second sensing means includes:

means for generating a first electrical signal in response to intensity variations of the first rectangular scanning light beam caused by B type defects and a second electrical signal in response to intensity variations of the second rectangular scanning light beam caused by point type defects; and means for passing predetermined values of the first and second signals to determine a predetermined size range of the B type and point type defects, respectively.

11. The glass inspecting apparatus as set forth in claim 10 wherein the generating means includes:

an elliptical specular surface;

reflecting means mounted at a first focal point of the specular surface on one side of the glass;

light beam incident on the reflecting means and reflected onto and from the specular surface through the glass toward the second focal point of the specular surface; and means for moving the reflecting means relative to the specular surface to displace the light beam along the specular surface and along the scan path;

said splitting means is a beam splitter; and further including:

means for locating the position of B type and point type defects in the glass; and means for mounting said first and second sensing means at a distance from the specular surface approximately equal to the second focal length of the specular surface.

12. The glass inspecting apparatus as set forth in claim 11 wherein the glass is a glass ribbon.

13. The glass inspecting apparatus as set forth in claim 11 wherein the glass is a glass sheet.

* * * * *